United States Patent [19]

Martin et al.

[11] Patent Number: 4,652,567
[45] Date of Patent: Mar. 24, 1987

[54] BENZO(C)-1,5-NAPHTHYRIDINES USEFUL FOR TREATING A PATIENT HAVING DRUG INDUCED MEMORY IMPAIRMENT IN NEED OF MEMORY ENHANCEMENT

[75] Inventors: Lawrence L. Martin, Lebanon; Linda L. Setescak, Somerville; Susan J. Scott, No. Brunswick, all of N.J.

[73] Assignee: Hoechst-Roussel Pharmaceuticals Inc., Somerville, N.J.

[21] Appl. No.: 711,327

[22] Filed: Mar. 13, 1985

[51] Int. Cl.$^4$ .................. A61K 31/435; C07D 401/04
[52] U.S. Cl. .................. 514/254; 514/292; 544/361; 546/81; 546/94; 546/111; 548/428
[58] Field of Search .................. 544/361; 546/81; 514/254, 292

[56] References Cited

FOREIGN PATENT DOCUMENTS 13666   7/1980  European Pat. Off. ............ 514/292
2273533 1/1976  France .
2040682 9/1980  United Kingdom ................ 514/292

OTHER PUBLICATIONS

Kolocouris & Rigo; Chimika Chronika, New Series 11, 309 (1982).
Rigo & Kolocouris, J. Heterocyclic Chem 20, 893, 1983.
Rigo, Fossaet, de Quilarg & Kolocouris, J. Heterocyclic Chem. 21, 1381 (1984).
Ferlux, Chem Abst. 85-32835x, eq. France Pat. No. 2273533.
Bauer & Hewitson, J. Org. Chem. 27, 3982 (1962).
Thyagarjan, Mechanism of Molecular Migrations, 1971, pp. 251-289.
Campaigne, Mathews, J. Heterocyclic Chem. 12, 391 (1975).

Primary Examiner—Donald G. Daus
Assistant Examiner—Cecilia Shen
Attorney, Agent, or Firm—Tatsuya Ikeda

[57] ABSTRACT

There are disclosed novel compounds of the formula

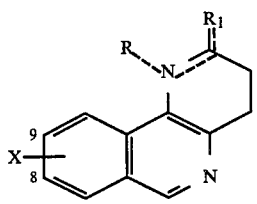

where X is H, halogen, loweralkyl, loweralkoxy, —CF$_3$, or —OH; R is H, loweralkyl, arylloweralkyl, diarylloweralkyl, loweralkanoyl, arylloweralkanoyl or diarylloweralkanoyl; and R$_1$ is H$_2$, O or —NR$_2$R$_3$, R$_2$ and R$_3$ being independently H or loweralkyl, or taken together with the nitrogen atom to which they are attached constitute

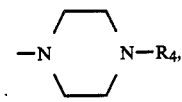

R$_4$ in turn being H, loweralkyl, hydroxyloweralkyl, aryl, arylloweralkyl or diarylloweralkyl or pharmaceutically acceptable acid addition salts thereof, which are useful for enhancing memory.

65 Claims, No Drawings

BENZO(C)-1,5-NAPHTHYRIDINES USEFUL FOR TREATING A PATIENT HAVING DRUG INDUCED MEMORY IMPAIRMENT IN NEED OF MEMORY ENHANCEMENT

This invention relates to novel compounds of the formula

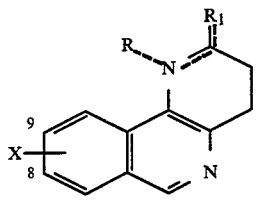

where X is H, halogen, loweralkyl, loweralkoxy, —$CF_3$, or —OH; R is H, loweralkyl, arylloweralkyl, diarylloweralkyl, loweralkanoyl, arylloweralkanoyl or diarylloweralkanoyl; and $R_1$ is $H_2$, O or —$NR_2R_3$, $R_2$ and $R_3$ being independently H or loweralkyl, or taken together with the nitrogen atom to which they are attached constitute

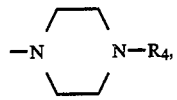

$R_4$ in turn being H, loweralkyl, hydroxyloweralkyl, aryl, arylloweralkyl or diarylloweralkyl or pharmaceutically acceptable acid addition salts thereof, which are useful for enhancing memory, methods for synthesizing them, pharmaceutical compositions comprising an effective memory enhancing amount of such a compound and methods of treating a patient in need of memory enhancement by administering such a compound to the patient.

This invention also relates to novel compounds of the formula

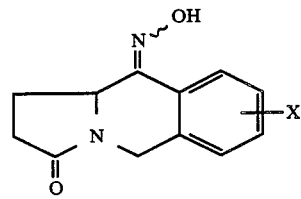

where X is as defined above, which are useful as an intermediate for synthesizing compounds I.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shell mean a phenyl group having 0, 1, 2 or 3 substituents each of which being independently loweralkyl, loweralkoxy, halogen or $CF_3$, and the term diaryl shall mean two such aryl groups each of which being independent of the other.

The term loweralkanoyl shall mean a group obtained by removing a hydroxy group from the carboxyl group of a loweralkanoic acid, and thus it includes for instance formyl, acetyl and the like.

The term arylloweralkanoyl shall mean a loweralkanoyl group having an aryl substituent thereon, the terms loweralkanoyl and aryl having the respective meanings defined above.

The compounds of this invention are prepared by following one or more of the steps described below. Throughout the description of the synthetic steps, the definitions of X, R and $R_1$ through $R_4$ are as given above unless otherwise stated or indicated, and $R_5$ appearing below shall mean loweralkyl, arylloweralkyl or diarylloweralkyl and $R_6$ appearing below shall mean H, loweralkyl, arylloweralkyl or diarylloweralkyl.

STEP A

The compound of formula III below is cyclized to afford compound of formula IV below.

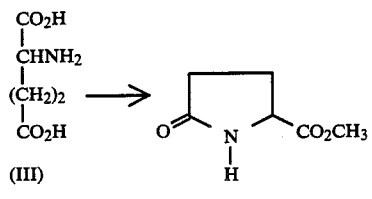

Said cyclization is typically conducted by refluxing an aqueous solution of compound III, followed by isolation and esterification with acidic methanol.

STEP B

Compound IV is reacted with a compound of formula V below in the presence of a strong base such as NaH to afford a compound of formula VI below.

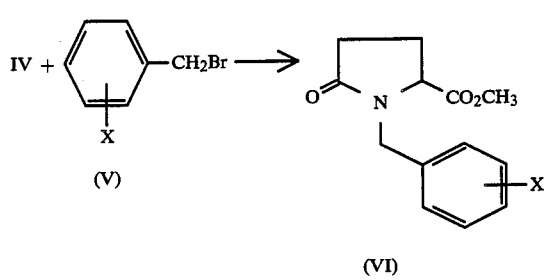

Said reaction is conveniently conducted in a suitable solvent such as an anhydrous aromatic compound, namely, toluene or the like at a temperature of about 80°–100° C.

STEP C

Compound VI is hydrolyzed to afford a compound of formula VII below.

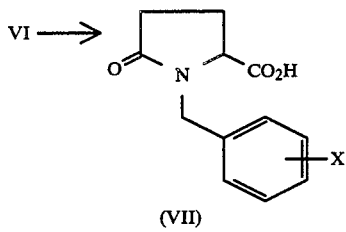

(VII)

Said hydrolysis is conveniently conducted in an aqueous system containing compound VI and an alkaline substance such as sodium hydroxide and heating the system with a steam bath.

STEP D

The carboxyl group of compound VII is converted to its acid chloride with a suitable agent such as thionyl chloride and the resultant acid chloride compound is cyclized under a Friedel-Crafts condition to afford a compound of the formula VIII below.

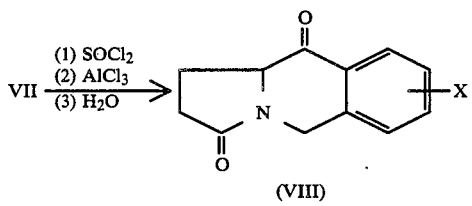

(VIII)

Said reaction is typically conducted by dissolving compound VII and thionyl chloride in a suitable solvent such as dichloromethane and refluxing the solution. The Friedel-Crafts reaction is typically conducted by adding $AlCl_3$ to the solution remaining after the acid chloride formation step and stirring the resultant mixture at or below the ambient temperature.

STEP E

Compound VIII is reacted with hydroxylamine to afford the aforementioned compound II.

Said oxime formation reaction is conveniently conducted, for instance, by preparing a suspension comprising compound VIII, hydroxylamine hydrochloride, water, ethanol and a weak base such as sodium acetate and refluxing the suspension.

STEP F

The oxime compound of the formula II is converted to a compound of the formula Ia below by heating it in a substantially anhydrous acidic medium.

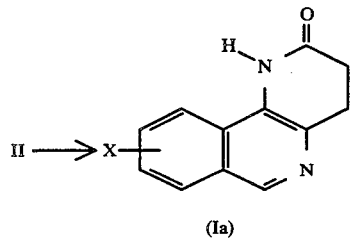

(Ia)

It is convenient to conduct the above reaction by adding compound II to a vigorously stirred large excess of polyphosphoric acid at a temperature of about 100°–150° C., but since this reaction may be considered a species of so-called Wolff-Semmler aromatization reaction (see for instance "Mechanisms of Molecular Migrations", Volume 4, edited by B. S. Thyagarajan, Wiley-Interscience, New York, 1971), other suitable reaction conditions used for Wolff-Semmler aromatization reactions may also be used to effect the above reaction step, including the use of so-called Beckmann's mixture which is a mixture of hydrogen chloride, acetic acid and acetic anhydride.

STEP G

Compound Ia is reacted with an amine of the formula $NHR_2R_3$ to afford a compound of the formula Ib below.

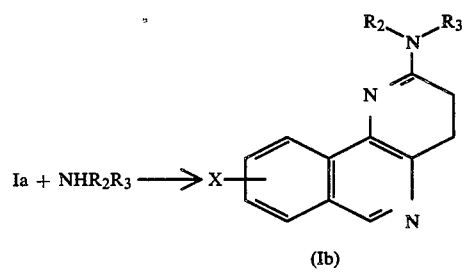

(Ib)

Said reaction is typically conducted in the presence of $TiCl_4$ and a suitable solvent such as anhydrous tetrahydrofuran at a temperature of about 0°–40° C.

STEP H

Compound Ia is reacted with a compound of the formula $R_5$-Hal where $R_5$ is as defined earlier and Hal is bromine, chlorine or iodine to afford a compound of the formula Ic below.

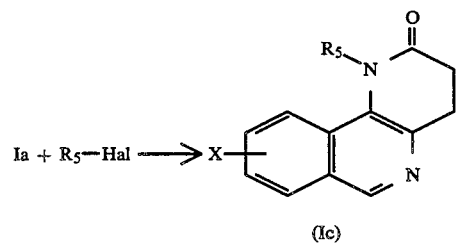

(Ic)

Said reaction is conducted typically in the presence of an acid scavenger such as KOH or the like in a suitable solvent such as dimethylsulfoxide at a temperature of about 20°–50°C.

STEP I

Compound Ia is reduced to afford a compound of the formula Id below.

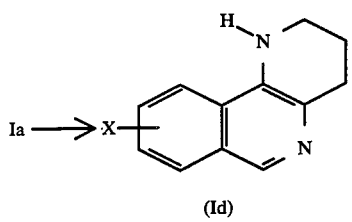

(Id)

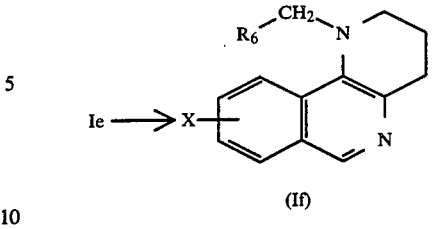

(If)

Said reduction is conducted for instance by reacting compound Ia with diborane in a suitable solvent such as anhydrous tetrahydrofuran at the ambient temperature or in the vicinity thereof.

STEP J

Compound Id is reacted with a compound of the formula $R_6COCl$, where Rhd is as defined earlier except that it is not hydrogen, to afford a compound of formula Ie below.

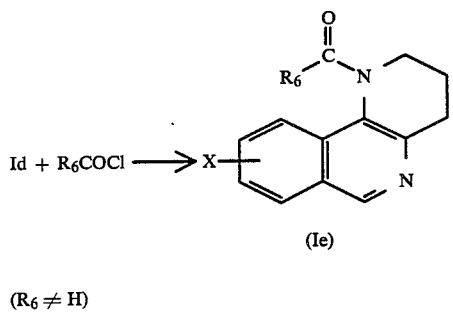

($R_6 \neq H$)

Said reaction is conveniently conducted in a suitable solvent such as pyridine or an excess of the acid chloride at a temperature of 20°14 50° C.

When $R_6$ is hydrogen, compound Ie is prepared by reacting compound Id with formic-acetic anhydride. Typically, the reaction is conducted by first preparing formic-acetic anhydride from acetic anhydride and concentrated formic acid (95-99% for instance) at about 40°-60° C. and then adding compound Id to the resultant solution and heating the reaction mixture at about 80°-100° C.

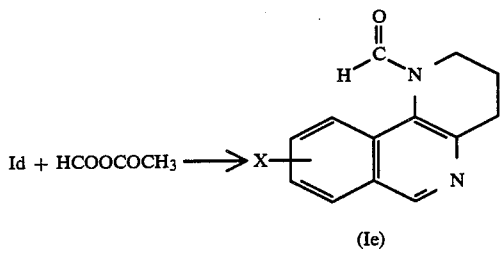

STEP K

Compound Ie where $R_6$ is as defined earlier including $R_6=H$, is reduced to afford a compound of formula If below.

Said reduction is conducted for instance by reacting compound Ie with diborane in a suitable solvent such as anhydrous tetrahydrofuran at the ambient temperature or in the vicinity thereof.

The naphthyridine compounds of formula I of the present invention are useful in the treatment of various memory dysfunctions characterized by decreased cholinergic function, such as Alzheimer's disease. This utility is manifested by the ability of these compounds to inhibit the enzyme acetyl cholinesterase and thereby increase acetylcholine levels in the brain.

Cholinesterase Inhibition Assay

The ability to inhibit acetylcholinesterase was determined by the photometric method of Ellman et al., Biochem. Pharmacol. 7, 88 (1961).

| Compound | Cholinesterase Inhibition $IC_{50}$ (molar) |
|---|---|
| 1,2,3,4-Tetrahydrobenzo[c]-1,5-naphthyridine | $6.1 \times 10^{-5}$ |
| 3,4-Dihydro-2-(4-methyl-1-piperazinyl)benzo[c]-1,5-naphthyridine hemihydrate | $8.4 \times 10^{-4}$ |
| 1-(Phenylacetyl)-1,2,3,4-tetrahydrobenzo[c]-1,5-naphthyridine | $3.2 \times 10^{-4}$ |
| (prior art compounds) | |
| 9-amino-1,2,3,4-tetrahydroacridine (tacrine) | $5.7 \times 10^{-6}$ |
| Physostigmine | $9.2 \times 10^{-8}$ |

This utility is further demonstrated by the ability of these compounds to restore cholinergically deficient memory in the Dark Avoidance Assay, where they are in general active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic agent that is known to cause memory impairment, is administered before an animal's initial exposure to the test chamber, the animal re-enters the dark compartment shortly after being placed in the test chamber 24 hours later. This effect of scopolamine is blocked by an active test compound, resulting in greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose (mg/kg of Body Weight) | % of Animals Greater than Scopolamine |
|---|---|---|
| 1,2,3,4-Tetrahydro- | 1.25 | 27 |
| benzo[c]-1,5-naphthyridine | 2.5 | 25 |
| (prior art compounds) | | |
| Tacrine | 0.63 | 13 |
| Pilocarpine | 5.0 | 13 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid additon salts of the invention include inorganic acids such as hydrochloric, hydrobromic, sulfuric, nitric, phosphoric and perchloric acids, as well as organic acids such as tartaric, citric, acetic, succinic, malic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contian, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention (including intermediate compounds which are believed to be novel) include:

($\pm$)-1-[(3-Fluorophenyl)methyl]-5-methoxycarbonyl-2-pyrrolidinone;
($\pm$)-1-[(3-Chlorophenyl)methyl]-5-methoxycarbonyl-1-pyrrolidinone;
($\pm$)-1-[(4-Methoxyphenyl)methyl]-5-methoxycarbonyl-2-pyrrolidinone;
($\pm$)-1-[(3-Methylphenyl)methyl]-5-methoxycarbonyl-2-pyrrolidinone;
($\pm$)-1-[(3-Fluorophenyl)methyl]-5-oxo-2-pyrrolidinecarboxylic acid;
($\pm$)-1-[(3-Chlorophenyl)methyl]-5-oxo-2-pyrrolidinecarboxylic acid;
($\pm$)-1-[(4-Methoxyphenyl)methyl]-5-oxo-2-pyrrolidinecarboxylic acid;
($\pm$)-1-[(3-Methylphenyl)methyl]-5-oxo-2-pyrrolidinecarboxylic acid;
1,10a-Dihydropyrrolo[1,2-b]isoquinoline-3,10[2H,5H]-dione;
1,10a-Dihydro-7-fluoropyrrolo[1,2-b]isoquinoline-3,10[2H,5H]-dione;
7-Chloro-1,10a-dihydropyrrolo[1,2-b]isoquinoline-3,10[2H,5H]-dione;
1,10a-Dihydro-8-methoxypyrrolo[1,2-b]isoquinoline-3,10[2H,5H]-dione;
9-Chloro-1,10a-dihydropyrrolo[1,2-b]isoquinoline-3,10[2H,5H]-dione;
1,10a-Dihydropyrrolo[1,2-b]isoquinoline-3,10[2H,5H]-dione oxime;
7-Chloro-1,10a-dihydropyrrolo[1,2-b]isoquinoline-3,10[2H,5H]-dione oxime;
8-Chloro-1,10a-dihydropyrrolo[1,2-b]isoquinoline-3,10[2H,5H]-dione oxime;
9-Chloro-1,10a-dihydropyrrolo[1,2-b]isoquinoline-3,10[2H,5H]-dione oxime;
1,10a-Dihydro-8-methoxypyrrolo[1,2-b]isoquinoline-3,10[2H,5H]-dione oxime;
1,10a-Dihydro-7-methylpyrrolo[1,2-b]isoquinoline-3,10[2H,5H]-dione oxime;
1,4-Dihydrobenzo[c]-1,5-naphthyridin-2(3H)-one;
8-Chloro-1,4-dihydrobenzo[c]-1,5-naphthyridin-2(3H)-one;

9-Chloro-1,4-dihydrobenzo[c]-1,5-naphthyridin-2(3H)-one;
3,4-Dihydro-2-methylaminobenzo[c]-1,5-naphthyridine;
3,4-Dihydro-2-(4-methyl-1-piperazinyl)benzo[c]-1,5-naphthyridine hemihydrate;
1,4-Dihydro-1-phenylmethylbenzo[c]-1,5-naphthyridin-(3H)-one;
1,2,3,4-Tetrahydrobenzo[c]-1,5-naphthyridine;
8-Chloro-1,2,3,4-tetrahydrobenzo[c]-1,5-naphthyridine;
9-Chloro-1,2,3,4-tetrahydrobenzo[c]-1,5-naphthyridine;
8-Fluoro-1,2,3,4-tetrahydrobenzo[c]-1,5-naphthyridine;
9-Methoxy-1,2,3,4-tetrahydrobenzo[c]-1,5-naphthyridine;
1-Formyl-1,2,3,4-tetrahydrobenzo[c]-1,5-naphthyridine;
1-Benzoyl-1,2,3,4-tetrahydrobenzo[c]-1,5-naphthyridine;
1-(Phenylacetyl)-1,2,3,4-tetrahydrobenzo[c]-1,5-naphthyridine;
1-Methyl-1,2,3,4-tetrahydrobenzo[c]-1,5-naphthyridine dihydrochloride;
1-(2-Phenylethyl)-1,2,3,4-tetrahydrobenzo[c]-1,5-naphthyridine; and
1-phenylmethyl-1,2,3,4-tetrahydrobenzo[c]-1,5-naphthyridine.

The following examples are shown for the purpose of illustrating the present invention.

EXAMPLE 1

(±)-1-[(3-Fluorophenyl)methyl]-5-methoxycarbonyl-2-pyrrolidinone

Sodium hydride (24.00 g as a 50% dispersion in mineral oil) was washed with sieve dried toluene (3×100 ml). Sieve dried toluene (500 ml) was then added to the NaH and the stirred suspension was treated dropwise over 45 minutes with a solution of (±)-methyl pyroglutamate (71.58 g) in sieve dried toluene (50 ml). The flask was immersed during this time in an oil bath which served as a heat sink. After the addition of the (±)-methyl pyroglutamate solution was complete, the internal temperature of the flask was raised to 65° C. and maintained there for 30 minutes. The flask was then cooled to the ambient temperature and the solution was treated dropwise over 10 minutes with a solution of 3-fluorobenzyl bromide (100 g) in sieve dried toluene (50 ml). After the addition was complete, the internal temperature of the flask was raised to 90° C. and maintained there until a thin layer chromatographic analysis (TLC analysis hereafter) using silica gel and ethyl acetate indicated the absence of the starting material. While still hot, the suspension was vacuum filtered through a Celite pad and concentrated to an oil (90 g) which solidified on standing. The solid was recrystallized from hexane (100 ml) to afford 78.69 g of nearly pure crystals, m.p. 46°–51° C. A 6 g sample was recrystallized from hexane (30 ml) to give 5.31 g of crystals, m.p. 52°–55° C.

ANALYSIS: Calculated for $C_{13}H_{14}FNO_3$: 62.12% C; 5.62% H; 5.58% N. Found: 61.72% C; 5.55% H; 5.60% N.

EXAMPLE 2

(±)-1-[(3-Chlorophenyl)methyl]-5-methoxycarbonyl-2-pyrrolidinone

Sodium hydride (23.38 g of a 50% dispersion in mineral oil) was washed with sieve dried toluene. Sieve dried toluene (1000 ml) was then added to the NaH and the stirred suspension was treated dropwise over 45 minutes with a solution of (±)-methyl pyroglutamate (63.0 g) in sieve dried toluene (75 ml). The flask was immersed during this time in an oil bath which served as a heat sink. After the addition of the (±)-methyl pyroglutamate solution was complete, the bath temperature was raised to 65° C. After heating for 30 minutes, the oil bath was removed and the solution was treated dropwise over 10 minutes with a solution of 3-chlorobenzyl bromide (100 g) in sieve dried toluene (50 ml). After the addition was complete, the oil bath was replaced and the solution was heated for 2 hours at 100° C. Celite was then added to the mixture and while still hot, the mixture was vacuum filtered through a Celite pad. The filtrate was concentrated to an oil which was stored in a refrigerator under nitrogen.

Purification of 11.20 g of the oil by high performance liquid chromatography (HPLC, hereafter) using silica gel column and methanol gave 8.10 g of an oil. The sample was dried in an Abderhalden pistol over toluene.

ANALYSIS: Calculated for $C_{13}H_{14}ClNO_3$: 58.33% C; 5.27% H; 5.23% N. Found: 58.13% C; 5.30% H; 5.17% N.

EXAMPLE 3

(±)-1-[(4-Methoxyphenyl)methyl]-5-methoxycarbonyl-2-pyrrolidinone

Sodium hydride (27.84 g of a 50% dispersion in mineral oil) was washed with sieve dried toluene (3×100 ml). Sieve dried toluene (500 ml) was then added to the NaH and the stirred suspension was treated dropwise over 45 minutes with a solution of (±)methyl pyroglutamate (83.03 g) in sieve dried toluene (50 ml). The flask was immersed during this time in an oil bath which served as a heat sink. After the addition of the (±)methyl pyroglutamate solution was complete, the bath temperature was raised to 80° C. (internal temperature 65° C.). After heating for 30 minutes, the flask was cooled to room temperature and the solution was treated dropwise over 10 minutes with a solution of 4-methoxybenzyl chloride (100 g) in sieve dried toluene (50 ml). After the addition was complete, the mixture was heated to 85° C. (internal temperature). While still hot, the mixture was vacuum filtered and the filtrate was concentrated to an oil.

Purification of 10 g of the oil was accomplished by HPLC (silica gel column, eluted with ethyl acetate) to give 4.85 g of an oil. The sample was dried in an Abderhalden pistol over toluene.

ANALYSIS: Calculated for $C_{14}H_{17}NO_4$: 63.84% C; 6.51% H; 5.32% N. Found: 63.62% C; 6.71% H; 5.04% N.

EXAMPLE 4

(±)-1-[(3-Fluorophenyl)methyl]-5-oxo-2-pyrrolidinecarboxylic acid

A solution of 19.00 g of sodium hydroxide pellets in 225 ml of water was treated with 115.52 g of (±)-1-[(3-fluorophenyl)methyl]-5-methoxycarbonyl-2-pyrrolidinone and the mixture was heated for four hours (steam bath). The solution was cooled to the ambient temperature and extracted with diethyl ether (3×250 ml). The aqueous phase was acidified with concentrated hydrochloric acid to about pH=1. The aqueous phase was extracted with dichloromethane (2×300 ml) and the combined organic phase was dried over $Na_2SO_4$. The solution was vacuum filtered and the filtrate was concentrated to an oil which solidified on standing. The solid was recrystallized from 300 ml of toluene to yield 72.16 g of crystals, m.p. 114°–116.5° C.

ANALYSIS: Calculated for $C_{12}H_{12}FNO_3$: 60.73% C; 5.10% H; 5.91% N. Found: 60.51% C; 5.20% H; 5.77% N.

EXAMPLE 5

(±)-1-[(3-Chlorophenyl)methyl]-5-oxo-2-pyrrolidinecarboxylic acid

A solution of 16.00 g of sodium hydroxide pellets in 165 ml of water was treated with 99.01 g of (±)-1-[(3-chlorophenyl)methyl]-5-methoxycarbonyl-2-pyrrolidinone and was heated for two hours with a steam bath. The solution was cooled to room temperature and extracted with diethyl ether (2×300 ml). The aqueous phase was acidified with 45 ml of concentrated hydrochloric acid and extracted with dichloromethane (3×200 ml). Crystals precipitated out of the dichloromethane. The crystals (80.21 g, damp with solvent) were dried overnight at 65° C. under vacuum.

The solid was recrystallized from 800 ml of toluene to give 54.72 g of crystals m.p. 144°–146° C. The crystals were dried overnight at 85° C. under vacuum.

ANALYSIS: Calculated for $C_{12}H_{12}ClNO_3$: 56.79% C; 4.77% H; 5.53% N. Found: 57.05% C; 4.80% H; 5.49% N.

EXAMPLE 6

(±)-1-[(4-Methoxyphenyl)methyl]-5-oxo-2-pyrrolidinecarboxylic acid

A solution of 16.80 g of sodium hydroxide pellets in 175 ml of water was treated with 75 g of (±)-1-[(4-methoxyphenyl)methyl]-5-methoxycarbonyl-2-pyrrolidinone and the mixture was heated for two hours with a steam bath. The solution was cooled to room temperature and extracted with diethyl ether (2×300 ml). The aqueous phase was acidified to about pH=1 with 50 ml of concentrated hydrochloric acid and extracted with dichloromethane (3×250 ml). The dried ($Na_2SO_4$) organic phase was vacuum filtered and concentrated to an oil which solidified on standing (80 g). The solid was recrystallized from toluene (300 ml) to give 34.18 g of crystals, m.p. 103°–104.5° C.

ANALYSIS: Calculated for $C_{13}H_{15}NO_4$: 62.62% C; 6.07% H; 5.62% N. Found: 62.48% C; 6.05% H; 5.54% N.

EXAMPLE 7

1,10a-Dihydropyrrolo[1,2-b]isoquinoline-3,10[2H,5H]-dione

To a solution prepared from 11.68 g of (+)-N-benzylpyroglutamic acid (See E. Campaigne and D. P. Matthews, J. Het. Chem., 12, 391 (1975)), 100 ml of $CH_2Cl_2$ and a drop of dimethylformamide (DMF), 7.57 g of $SOCl_2$ was added dropwise. The mixture was refluxed for five hours and allowed to stand overnight at ambient temperature. The reaction mixture was cooled in an ice-salt bath. Aluminum chloride (22.6 g) was added in portions with exclusion of moisture and vigorous stirring. The temperature did not exceed 10° C. during the addition. The mixture was stirred 1.5 hours and then ice was added gradually. The mixture was partitioned between water and $CH_2Cl_2$. The $CH_2Cl$ phase was washed with water, dried ($Na_2SO_4$), filtered and evaporated to give 10 g of a crude product. Recrystallization from toluene gave 7.45 g of crystals, m.p. 103°–105° C.

ANALYSIS: Calculated for $C_{12}H_{11}NO_2$: 71.62% C; 5.51% H; 6.96% N. Found: 71.36% C; 5.43% H; 6.85% N.

EXAMPLE 8

1,10a-Dihydro-7-fluoropyrrolo[1,2-b]isoquinoline-3,10[2H,5H]-dione

To a solution of 50.00 g of (±)-1-[(3-fluorophenyl)methyl]-5-oxo-2-pyrrolidine carboxylic acid in sieve dried dichloromethane (450 ml), 27.48 g of thionyl chloride was added, and the resultant solution was stirred and refluxed for 5 hours. An infrared spectrum of the solution indicated the presence of the acid chloride. After standing overnight at ambient temperature, the solution was chilled to 5° C. and 84 g of aluminum chloride was added in portions with vigorous stirring. The reaction was exothermic and there was a slow evolution of gas. The mixture was stirred at ambient temperature for 3 hours. The reaction was quenched by the addition of ice chips and water. The two phases of the mixture were separated and the aqueous phase was extracted with dichloromethane (4×150 ml). The combined organic phase was dried ($Na_2SO_4$) and concentrated to a solid (69.73 g).

The solid was purified by HPLC (silica gel, eluted with ethyl acetate) to give 37.23 g of the 7-fluoro isomer and 4 g of the 9-fluoro isomer. The 7-fluoro isomer was recrystallized from ethyl acetate (400 ml) to afford 28.63 g of crystals, m.p. 160°–163° C.

ANALYSIS: Calculated for $C_{12}H_{10}FNO_2$: 65.70% C; 4.60% H; 6.39% N Found: 65.60% C; 4.68% H; 6.27% N.

EXAMPLE 9

7-Chloro-1,10a-dihydropyrrolo[1,2-b]isoquinoline-3,10[2H,5H]-dione

To a solution of 25.37 g of (±)-1-[(3-chlorophenyl)methyl]-5-oko-2-pyrrolidinecarboxylic acid in sieve dried dichloromethane (20 ml), 13.09 g of thionyl chloride was added, and the resultant solution was stirred and refluxed with the exclusion of moisture for 6 hours. An infrared spectrum of the solution indicated the presence of the acid chloride. After standing overnight at ambient temperature, the solution was chilled to 5° C. and 40 g of aluminum chloride was added in portions with exclusion of moisture and vigorous stirring. The reaction was slightly exothermic and a solid began to precipitate. The flask was heated intermittently with a steam bath to increase the rate of the reaction. After each heating, the gas evolution was allowed to subside. When heating did not produce gas evolution, ice chips were added to quench the reaction. Water was then added to the mixture and the phases were separated. The aqueous phase was extracted with dichloromethane and the combined organic phase was dried ($Na_2SO_4$). The mixture was vacuum filtered and the resultant mixture was vacuum filtered to give 11.56 g of a solid. The solid was dried overnight under vacuum.

The ethyl acetate washings were concentrated to 10.30 g of a solid. A TLC analysis (silica, ethyl acetate) showed that the compositions of the two crops of solid were the same. The combined solid was purified by HPLC (silica gel, eluted with ethyl acetate) to give 16.35 g of a solid which was recrystallized from ethyl acetate (250 ml) to yield 12.0 g of a solid, m.p. 150.5°–154° C.

ANALYSIS: Calculated for $C_{12}H_{10}ClNO_2$: 61.16% C; 4.28% H; 5.94% N; Found: 60.79% C; 4.41% H; 5.89% N.

EXAMPLE 10

Chloro-1,10a-dihydropyrrolo[1,2-b]isoquinoline-3,10[2H,5H]-dione

9-Chloro-1,10a-dihydropyrrolo[1,2-b]isoquinoline-3,10[2H,5H]-dione was isolated by HPLC (silica gel, ethyl acetate) as the minor product from the reaction which afforded 7-chloro-1,10a-dihydropyrrolo[1,2-b]isoquinoline-3,10[2H,5H]-dione. From two runs of the reaction, a total of 3.55 g of the 9-chloro isomer was obtained and recrystallized from 100 ml of ethyl acetate to afford 2.03 g of crystals, m.p 198°–202° C.

ANALYSIS: 8 Calculated for $C_{12}H_{10}ClNO_2$: 61.16% C; 4.28% H; 5.94% N; Found: 60.79% C; 4.38% H; 5.83% N.

EXAMPLE 11

1,10a-Dihydropyrrolo[1,2-b]isoquinoline-3,10[2H,5H]-dione oxime

A mixture consisting of 2.5 g of 1,10a-dihydropyrrolo[1,2-b]isoquinoline-3,10[2H,5H]-dione in 20 ml of 95% ethanol (EtOH), 1.72 g of hydroxylamine hydrochloride in 10 ml of water and 3.7 g of sodium acetate trihydrate in 10 ml of water was refluxed for 7 hours and thereafter allowed to stand overnight at ambient temperature. The product crystallized from the reaction mixture to give 2.2 g of crystals. Recrystallization from 95% EtOH gave 1.4 g of crystals, m.p. 206°–209° C.

ANALYSIS: Calculated for $C_{12}H_{12}N_2O_2$: 66.65% C; 5.60% H; 12.95% N; Found: 66.36% C; 5.59% H; 12.93% N.

EXAMPLE 12

7-Chloro-1,10a-dihydropyrrolo[1,2-b]isoquinoline-3,10[2H,5H]-dione oxime

A suspension of 9.00 g of 7-chloro-1,10a-dihydropyrrolo[1,2-b]isoquinoline-3,10[2H,5H]-dione in 95% ethanol (65 ml) was treated with a premixed solution prepared from 10.40 g of sodium acetate trihydrate in water (35 ml) and 5.31 g of hydroxylamine hydrochloride in water (35 ml). The suspension was heated to reflux and after 10 minutes a solution formed. After 1 hour of refluxing, a precipitate began to form and heating was continued for another 1.5 hours, after which time the mixture was allowed to cool to ambient temperature. The precipitate was isolated by vacuum filtration and dried under vacuum at 40° C. The solid was recrystallized form n-propanol (300 ml) to give 6.45 g of crystals, m.p. 249°–252° C.

ANALYSIS: Calculated for $C_{12}H_{11}ClN_2O_2$: 57.50% C; 4.42% H; 11.17% N; Found: 57.33% C; 4.51% H; , 11.11% N.

EXAMPLE 13

8-Chloro-1,10a-dihydropyrrolo[1,2-b]isoquinoline-3,10[2H,5H]-dione oxime

A stirred suspension of 12.65 g of 8-chloro-1,10adihydropyrrolo[1,2-b]isoquinoline-3,10[2H,5H]-dione (prepared in substantially the same manner as the 7-chloro compound in Example 12, m.p. 130°–136° C.) in 95% ethanol (85 ml) was treated with a premixed solution prepared from sodium acetate trihydrate (14.56 g) in water (48 ml) and hydroxylamine hydrochloride (7.44 g) in water (48 ml). The stirred suspension was heated to reflux, during which a solution formed followed by separation of a crystalline precipitate. After 2 hours of refluxing, the mixture was cooled and the precipitate was collected and washed twice with 50% aqueous ethanol. Drying at 40° C. overnight in vacuo gave 10.95 g of a solid, m.p. 227.5°–230.5° C. Recrystallization of the solid from n-propanol (300 ml) afforded 8.56 g of crystals, m.p. 229°–235° C.

ANALYSIS: Calculated for $C_{12}H_{11}ClN_2O_2$: 57.50% C; 4.42% H; 11.17% N; Found: 57.18% C; 4.41% H; 11.21% N.

EXAMPLE 14

9-Chloro-1,10a-dihydropyrrolo[1,2-b]isoquinoline-3,10[2H,5H]-dione oxime

A suspension of 1.00 g of 9-chloro-1,10a-dihydropyrrolo[1,2-b]isoquinoline-3,10[2H,5H]-dione in 95% ethanol (10 ml) was treated with a premixed solution prepared from 1.17 g of sodium acetate trihydrate in water (5 ml) and 0.60 g of hydroxylamine hydrochloride in water (5 ml). The suspension was heated to reflux and after 15 minutes a solution formed. After 1 hour of reflux, a precipitate began to form. Heating was continued for another 1.5 hours, after which time the mixture was allowed to cool to ambient temperature. The precipitate was isolated by vacuum filtration and dried under vacuum at 40° C.

The solid (0.75 g) was combined with 0.92 g of a material obtained in similar manner and recrystallized from 95% ethanol (100 ml) to afford 1.25 g of crystals, m.p. 260°–265° C.

ANALYSIS: Calculated for $C_{12}H_{11}ClN_2O_2$: 57.50% C; 4.42% H; 11.17% N;, Found: 57.55% C; 4.40% H; , 11.04% N.

EXAMPLE 15

1,4-Dihydrobenzo[c]-1,5-naphthyridin-2(3H)-one

To 300 g of vigorously stirred polyphosphoric acid warmed to 115° C., 10 g of 1,10a-dihydropyrrolo[1,2-b]isoquinoline-3,10[2H,5H]-dione oxime was added. The mixture was held at this bath temperature for 10 minutes. The internal temperature rose to 135°–140° C. The mixture was then poured into 1500 ml of ice water, and the mixture was basified with 50% NaOH to about pH=8 and the resultant crystalline precipitate was collected to give 7.14 g of crude product Chromatography on a silica gel column, using ethyl acetate gave 4.8 g of pure product, m.p. 225° C.

ANALYSIS: Calculated for $C_{12}H_{10}N_2O$: 72.69% C; 5.08% H; 14.13% N;

Found: 72.53% C; 5.26% H; 14.14% N.

EXAMPLE 16

8-Chloro-1,4-dihydrobenzo[c]-1,5-naphthyridin-2(3H)-one

To 110 g of vigorously stirred polyphosphoric acid, which had been heated to 105° C., 10.21 g of 7-chloro-1,10a-dihydropyrrolo[1,2-b]isoquinoline-3,10[2H,5H]-dione oxime was added. The bath temperature was held at 105° C. for 25 minutes. On addition of the oxime, however, the internal temperature rose to 145° C. The reaction was quenched by pouring the mixture into 800 ml of water and subsequently another 300 ml of water was added to the mixture. The mixture was basified to about pH=11 with 50% sodium hydroxide at which point precipitate began to separate from the mixture. Due to a large amount of inorganic phosphate salts formed, the mixture was diluted with water to approximately 20 liters. The precipitate was collected by vacuum filtration and dried overnight under vacuum at 60° C.

The solid was recrystallized from 1200 ml of n-propanol to afford 6.1 g of crystals, m.p. 281°–284° C. The crystals were dried under vacuum overnight at 50° C.

ANALYSIS: Calculated for $C_{12}H_9ClN_2O$: 61.89% C; 3.90% H; 12.04% N; Found: 62.00% C; 3.97% H; 12.00% N.

EXAMPLE 17

9-Chloro-1,4-dihydrobenzo[c]-1,5-naphthyridin-2(3H)-one

To stirred hot (100° C.) polyphosphoric acid (70 g) was added finely powdered 8-chloro-1,10a-dihydropyrrolo[1,2-b] isoquinoline-3,10[2H,5H]-dione oxime (5.01 g) in one portion. An exothermic reaction initiated and quickly subsided. Fourteen minutes after the addition of the oxime, the reaction mixture was decanted into water (250 ml). The suspension was diluted with water to approximately 400 ml of total volume and basified with 50% sodium hydroxide solution with cooling. The mixture was extracted with $CH_2Cl_2$ (2000 ml), dried ($Na_2SO_4$), filtered and concentrated to give 5.3 g of a solid. The material was purified by HPLC (silica gel, eluted with ethyl acetate) to give 4.5 g of a solid. Recrystallization from n-propanol gave 2.92 g of crystals, m.p 285°–286° C.

ANALYSIS: Calculated for $C_{12}H_9ClN_2O$: 61.95% C; 3.90% H; 12.04% N; Found: 61.97% C; 3.92% H; 11.99% N.

EXAMPLE 18

3,4-Dihydro-2-methylaminobenzo[c]-1,5-naphthyridine

A solution of anhydrous methylamine (30 ml), 1,4-dihydrobenzo[c]-1,5-naphthyridin-2(3H)-one (5.46 g) and sieve dried tetrahydrofuran (450 ml) was stirred and chilled with ice water, and was treated dropwise over 30 minutes with a preformed complex of titanium tetrachloride (3.0 ml, 5.2 g) and sieve dried tetrahydrofuran (220 ml). The resultant mixture was stirred with cooling for 1 hour, followed by stirring for 3.5 hours at ambient temperature. After standing overnight at ambient temperature the reaction was quenched with water (100 ml) and 10% NaOH solution (30 ml). The suspension was filtered and concentrated to give a biphasic residue (pH 10). The mixture was extracted with dichloromethane (2×200 ml) dried ($Na_2SO_4$), filtered and evaporated to dryness (residue wt: 7.66 g). The residue was purified by HPLC (silica gel, eluted with 10% (v/v) methanol in ethyl acetate). The appropriate fractions were concentrated to give 5.1 g of pure product which was recrystallized from toluene (35 ml) to afford 3.56 g of crystals, m.p. 144°–145° C.

ANALYSIS: Calculated for $C_{13}H_{13}N_3$: 73.91% C; , 6.20% H; Found 73.74% C; 6.15% H.

EXAMPLE 19

3,4-Dihydro-2-(4-methyl-1-piperazinyl)benzo[c]-1,5-naphthyridine hemihydrate

A complex of $TiCl_4$ and tetrahydrofuran was prepared by dropwise treatment via syringe of tetrahydrofuran (200 ml) with $TiCl_4$ (2.8 ml, 4.84 g) with stirring and ice water chilling (exclusion of moisture). The resultant suspension was treated with tetrahydrofuran (50 ml) to give a solution of the complex which was transferred to a dropping funnel (without side arm). A stirred, ice water chilled solution of 1,4-dihydrobenzo[c]-1,5-naphthyridine-2(3H)-one (3.39 g), tetrahydrofuran (275 ml) and 1-methylpiperazine (34 ml) was treated dropwise over 35 minutes with the $TiCl_4$-tetrahydrofuran complex with exclusion of moisture. The mixture was then stirred overnight at ambient temperature. The reaction was quenched by addition of water (100 ml) over approximately one minute. The resultant mixture was filtered through coarse-grade fluted filter paper and the filtrate was concentrated to remove the tetrahydrofuran. After basification with 10% NaOH and extraction with $CH_2Cl_2$ (2×250 ml), the dried ($Na_2SO_4$) organic phase was filtered and evaporated to afford an oil (5.17 g) which contained several components by TLC (silica gel, methanol) analysis. The oil was purified by HPLC (silica gel, eluted with methanol) to give 3.93 g of a viscous oil which appeared pure by TLC (silica gel, methanol). This sample and another sample prepared in a similar manner were combined and repurified by HPLC as described above to give 4.48 g of an oil which appeared pure by TLC (silica gel, methanol).

ANALYSIS: Calculated for $C_{17}H_{20}N_4 \cdot 0.5\ H_2O$: 70.56% C; 7.32% H; , Found: 70.05% C; 7.31% H.

EXAMPLE 20

1,4-Dihydro-1-phenylmethylbenzo[c]-1,5-naphthyridin-2(3H)-one

A stirred solution of 1,4-dihydrobenzo[c]-1,5naphthyridin-2(3H)-one (3.97 g) in dimethylsulfoxide (sieve dried, 80 ml) was treated sequentially with powdered potassium hydroxide (2.64 g of 85% KOH) and benzyl bromide (3.76 g). The solution was stirred for 1.5 hours at ambient temperature, transferred to a separatory funnel, diluted with water (400 ml) and extracted with ethyl acetate (2×250 ml). The organic phase was washed with water (2×200 ml) dried ($Na_2SO_4$), filtered and evaporated to give a solid (4.9 g). Recrystallization from 95% ethanol (32 ml) gave 3.35 g of crystals, m.p. 153.5–155.5° C.

ANALYSIS: Calculated for $C_{19}H_{16}N_2O$: 79.14% C; 5.59% H; 9.71% N; Found 78.95% C;, 5.65% H; 9.65% N.

EXAMPLE 21

1,2,3,4-Tetrahydrobenzo[c]-1,5-naphthyridine

A stirred solution of 1,4-dihydrobenzo[c]-1,5-naphthyridin-2(3H)-one (4.0 g) in sieve dried tetrahydrofuran (400 ml) was treated over a few minutes with 0.98M borane in tetrahydrofuran (62 ml) under a dry nitrogen atmosphere. The resultant suspension was stirred for 5 hours at ambient temperature during which time a solution formed. After standing overnight at ambient temperature the solution was treated with glacial acetic acid (16 ml) followed by stirring for several minutes. The solution was then treated with 10% sodium hydroxide solution (180 ml) to give a biphasic system. Concentration on a rotary evaporator to remove the tetrahydrofuan gave a suspension of a solid which was extracted with $CH_2Cl_2$ (2×800 ml). The combined, dried ($Na_2SO_4$) organic phase was concentrated to afford a solid (5.18 g, tentatively identified as a borane complex). A suspension of the solid in glacial acetic acid (15 ml) was treated gradually with concentrated HCl (50 ml). When the gas evolution ceased, the mixture was warmed for a few minutes and then stirred for 0.5 hour at ambient temperature. The solution was strained through glass wool, and the filtrate was diluted with ice (300 ml) and water (100 ml) and then made alkaline with 50% sodium hydroxide solution. The mixture was extracted with $CH_2Cl_2$, dried ($Na_2SO_4$), filtered and concentrated to dryness (3.7 g). Recrystallization from acetonitrile (20 ml) gave 1.97 g of a crystalline material which was combined with 2.01 g of a similarly prepared product. The material was purified by HPLC (silica gel, eluted with 5% methanol in ethyl acetate) to give 3.72 g of a solid. Recrystallization from acetonitrile (20 ml) afforded 3.01 g of crystals, m.p. 124.5°–127.5° C.

ANALYSIS: Calculated for $C_{12}H_{12}N_2$: 78.23% C; , 6.57% N; Found 77.91% C; 6.56% N.

EXAMPLE 22

9-Chloro-1,2,3,4-tetrahydrobenzo[c]-1,5-naphthyridine

A stirred suspension of 9-chloro-1,4-dihydrobenzo[c]-1,5-naphthyridin-2(3H)-one (5.82 g) in sieve dried tetrahydrofuran (600 ml) was treated rapidly with 1M borane in tetrahydrofuran (150 ml) and the resultant solution was stirred 48 hours at ambient temperature. The solution was treated dropwise with 10% sodium hydroxide solution (125 ml) (gas evolution noted), concentrated to remove the tetrahydrofuran and the residual suspension was filtered. The filter cake (a borane complex of the product) was suspended in glacial acetic acid (40 ml) and was treated under nitrogen with concentrated hydrochloric acid (35 ml, gas evolution noted). After stirring for 1 hour at ambient temperature the solution was decanted over crushed ice (500 ml), diluted with water (100 ml) and basified with 50% sodium hydroxide solution. The resultant suspension was extracted with dichloromethane (2×350 ml) and the combined dried ($Na_2SO_4$) organic phase was evaporated to afford a solid (5.84 g). A TLC analysis (silica gel, ethyl acetate) indicated the presence of a major product and three impurities. The material was purified by HPLC (silica gel, eluted with ethyl acetate) to afford 4.64 g of a purified material. Recrystallization from acetonitrile (125 ml) gave 3.54 g of needles, m.p. 185°–186° C.

ANALYSIS: Calculated for $C_{12}H_{11}ClN_2$: 65.91% C; 5.07% H; 12.81% N; Found: 65.88% C; 5.19% H; 12.90% N.

EXAMPLE 23

1-Formyl-1,2,3,4-tetrahydrobenzo[c]-1,5-naphthyridine

Formic-acetic anhydride was prepared by treating 30 ml of acetic anhydride with 13.5 ml of 95–97% formic acid and stirring the resultant solution at 50° C. for 40 minutes. 1,2,3,4-Tetrahydrobenzo[c]-1,5-naphthyridine (5.0 g) was added to the solution in one portion followed by heating at 86° C. for 3.5 hours. A vigorous gas evolution was noted during the first hour of heating. A TLC analysis (silica gel, 10% methanol in ethyl acetate) suggested the presence of the starting material and the solution was held at 100° C. overnight. The cooled reaction solution was decanted into 300 ml of ice water and basified with 50% NaOH solution. After $CH_2Cl_2$ extraction (2×150 ml), the combined and dried ($Na_2SO_4$) organic phase was filtered and concentrated to an oil which still contained the starting material by TLC analysis. The mixed anhydride prepared from acetic anhydride (60 ml) and 95–97% formic acid (27 ml) was added to the oil and the solution was stirred at 58° C. Again gas evolution was noted. The solution was stirred for 2 hours at 85° C. (gas evolution subsided) and then quenched as described above. A TLC analysis indicated the absence of the starting material. Recrystallization of the crude product (5.2 g) from hot toluene (10 ml) by diluting the filtered solution gradually with cyclohexane (45 ml) and seeding gave 3.02 g of crystals, m.p 85°–88° C.

ANALYSIS: Calculated for $C_{13}H_{12}N_2O$: 73.57% C; 5.70% H; 13.20% N; Found: 73.88% C; 5.99% H; 13.19% N.

EXAMPLE 24

1-Benzoyl-1,2,3,4-tetrahydrobenzo[c]-1,5-naphthyridine

A stirred solution of 1,2,3,4-tetrahydrobenzo[c]-1,5-naphthyridine (4.6 g) and KOH-dried pyridine (50 ml) was treated dropwise over one minute with benzoyl chloride (8.4 g). A crystalline precipitate formed. The stirred suspension was heated (steam bath) for 1.25 hours and the resultant solution was then stirred overnight at ambient temperature during which a crystalline precipitate formed. The mixture was decanted into water (200 ml), basified with 10% sodium hydroxide solution and extracted with dichloromethane. The dried ($Na_2SO_4$) organic phase was filtered and evaporated to dryness (7.47 g of crystalline solid). Recrystallization from toluene afforded 6.25 g of crystals, m.p. 208.5°–210.5° C. An aliquot of the material (4.81 g) was further purified by preparative HPLC (silica gel, eluted with ethyl acetate). The appropriate fractions were concentrated and the residue was recrystallized from toluene (100 ml) to give 4.14 g of crystals, m.p. 208°–210° C.

ANALYSIS: Calculated for $C_{19}H_{16}N_2O$: 79.14% C; 5.59% H; 9.71% N; Found: 79.08% C; 5.82% H; 9.58% N.

EXAMPLE 25

1-(Phenylacetyl)-1,2,3,4-tetrahydrobenzo[c]-1,5-naphthyridine 1,2,3,4-Tetrahydrobenzo[c]-1,5-naphthyridine (3.22 g) was treated with cold phenylacetyl chloride (35 ml). Most of the material dissolved and then a precipitate separated. The mixture was diluted with ether (50 ml), and the precipitate was isolated by vacuum filtration and washed twice with ether. The filter cake was dissolved in water (100 ml), and the solution was basified with 10% sodium hydroxide solution and extracted with dichloromethane (2×100 ml). The combined and dried ($Na_2SO_4$) organic phase was filtered and concentrated to an oil (5.4 g), which was purified by HPLC (silica gel, eluted with ethyl acetate). The appropriate fractions were combined and concentrated to an oil (4.76 g). Trituration with ether and seeding (seed crystals formed on the neck of the flask which contained the oil) gave 2.68 g of crystals, m.p. 88.5–89.5° C.

ANALYSIS: Calculated for $C_{20}H_{18}N_2O$: 79.45% C; 6.00% H; 9.26% N; Found: 79.50% C; 6.10% H; 9.25% N.

EXAMPLE 26

1-Methyl-1,2,3,4-tetrahydrobenzo[c]-1,5-naphthyridine dihydrochloride

A solution of 1-formyl-1,2,3,4-tetrahydrobenzo[c]-1,5-naphthyridine (9.6 g) in sieve dried tetrahydrofuran (1000 ml) was treated under nitrogen over 60 seconds with excess 1M borane-tetrahydrofuran complex (175 ml). After stirring for 48 hours at ambient temperature, the solution was treated dropwise with 10% sodium hydroxide solution (vigorous gas evolution during initial addition of NaOH) to give a biphasic liquid which was concentrated to remove the tetrahydrofuran. The residual oil-water mixture was extracted with $CH_2Cl_2$ ($2 \times 300$ ml) and the combined and dried ($Na_2SO_4$) organic phase was filtered and concentrated to an oil (a borane complex). A solution of the oil in glacial acetic acid (25 ml) was treated gradually with concentrated hydrochloric acid (35 ml) under $N_2$ purge. After stirring for 0.5 hours at ambient temperature, the solution was decanted onto ice chips (500 ml), diluted with water (300 ml) and made alkaline with 50% sodium hydroxide solution. Extraction with $CH_2Cl_2$ ($2 \times 300$ ml) and concentration of the dried ($Na_2SO_4$) organic phase gave a mobile oil (7.59 g). The oil contained three significant impurities and the desired product according to a TLC analysis (silica gel, ethyl acetate). Initial purification was conducted by HPLC (silica gel, eluted with ethyl acetate) to give 1.85 g of a two component oil (1,2,3,4-tetrahydrobenzo[c]-1,5-naphthyridine and the desired product). A further HPLC purification in a similar manner utilizing the recycle technique to optimize the separation gave 1.66 g of the product as an oil. The product was combined with 1.38 g of a similarily prepared material, and a methanol solution of the oils was treated with excess ethereal hydrogen chloride. Concentration of the resultant solution gave 3.44 g of a crude material which was recrystallized from absolute ethanol (150 ml) to give 0.82 g of crystals. Concentration of the mother liquor and recrystallization of the residue from absolute ethanol (100 ml) give 1.43 g of crystals. The two lots of the material were combined, after a TLC analysis (silica gel, methanol) had confirmed the identity, to give 2.25 g of crystals, m.p. 206°–209° C. (transition with gas evolution), 261°–274° C.

ANALYSIS: Calculated for $C_{13}H_{14}N_2 \cdot 2HCl$: 57.58% C; 5.95% H; 10.33% N; Found 57.52% C; 6.25% H; 10.23% N.

EXAMPLE 27

1-(2-Phenylethyl)-1,2,3,4-tetrahydrobenzo[c]-1,5-naphthyridine

A stirred solution of 1-(phenylacetyl)-1,2,3,4tetrahydrobenzo[c]-1,5-naphthyridine (5.11 g) in sieve dried tetrahydrofuran (300 ml) was treated rapidly with 1M borane in tetrahydrofuran (68 ml). The resultant solution was stirred overnight under a nitrogen atmosphere with exclusion of moisture and thereafter allowed to stand 24 hours. The reaction was quenched by dropwise addition of 10% sodium hydroxide solution (60 ml) and then concentrated to remove the tetrahydrofuran. The oil-aqueous phase mixture was further diluted with water (100 ml) and extracted with dichloromethane ($2 \times 200$ ml). The combined and dried ($Na_2SO_4$) organic phase was filtered and concentrated to a viscous oil (a borane complex of the product). A solution of the oil in glacial acetic acid (30 ml) was cautiously treated with concentrated hydrochloric acid (15 ml) under nitrogen (vigorous gas evolution noted). After stirring for 1 hour at ambient temperature the solution was decanted over crushed ice (500 ml), diluted with water (200 ml) and basified with 50% sodium hydroxide solution. The mixture was extracted with $CH_2Cl_2$ ($2 \times 250$ ml) and the combined and dried ($Na_2SO_4$) organic phase was filtered and concentrated to an oil (4.72 g). A TLC analysis (silica gel, ethyl acetate) indicated the oil was a mixture of the desired product and 1,2,3,4-tetrahydrobenzo[c]-1,5-naphthyridine. The mixture was separated by preparative HPLC (silica gel, eluted with ethyl acetate, overlap fractions repurified using new columns) to give 1.92 g of the product as a viscous oil which was combined with a similarly prepared material to give 2.52 g of pure product.

ANALYSIS: Calculated: 83.30% C; 6.99% H; Found: 83.08% C; 7.06% H.

We claim:

1. A compound having the formula

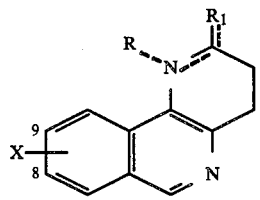

where X is H, halogen, loweralkyl, loweralkoxy, —$CF_3$ or —OH, R is H, loweralkyl, arylloweralkyl, diarylloweralkyl, loweralkanoyl, arylloweralkanoyl, diarylloweralkyl, loweralkanoyl, arylloweralkanoyl or diarylloweralkanoyl; and $R_1$ is $H_2$, O or —$NR_2R_3$, $R_2$ and $R_3$ being independently H or loweralkyl, or taken together with the nitrogen atom to which they are attached constitute

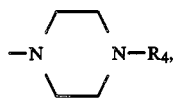

$R_4$ in turn being H, loweralkyl, hydroxyloweralkyl, aryl, arylloweralkyl or diarylloweralkyl or pharmaceutically acceptable acid addition salts thereof.

2. The compound as defined in claim 1, where $R_1$ is O.

3. The compound as defined in claim 2, where R is H.

4. The compound as defined in claim 3, where X is H, which is 1,4-dihydrobenzo[c]-1,5-naphthyridin-2(3H)-one.

5. The compound as defined in claim 3, where X is halogen.

6. The compound as defined in claim 5, where X is chlorine.

7. The compound as defined in claim 6, where X is 8-chloro, which is 8-chloro-1,4-dihydrobenzo[c]-1,5-naphthyridin-2(3H)-one.

8. The compound as defined in claim 6, where X is 9-chloro, which is 9-chloro-1,4-dihydrobenzo[c]-1,5-naphthyridin-2(3H)-one.

9. The compound as defined in claim 5, where X is fluorine.

10. The compound as defined in claim 3, where X is loweralkoxy.

11. The compound as defined in claim 10, where X is methoxy.

12. The compound as defined in claim 1, where R₁ is —NR₂R₃.

13. The compound as defined in claim 12, where R₂ is H and R₃ is loweralkyl.

14. The compound as defined in claim 13, where R₃ is methyl.

15. The compound as defined in claim 14, where X is H, which is 3,4-dihydro-2-methylaminobenzo[c]-1,5-naphthyridine.

16. The compound as defined in claim 14, where X is halogen.

17. The compound as defined in claim 14, where X is loweralkoxy.

18. The compound as defined in claim 12, where —NR₂R₃ is

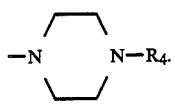

19. The compound as defined in claim 18, where R₄ is loweralkyl.

20. The compound as defined in claim 19, where R₄ is methyl.

21. The compound as defined in claim 20, where X is H, which is 3,4-dihydro-2-(4-methyl-1-piperazinyl)benzo[c]-1,5-naphthyridine.

22. The compound as defined in claim 21, where X is halogen.

23. The compound as defined in claim 21, where X is loweralkoxy.

24. The compound as defined in claim 2, where R is arylloweralkyl.

25. The compound as defined in claim 24, where R is phenylloweralkyl.

26. The compound as defined in claim 25, where R is

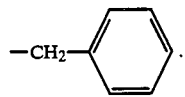

27. The compound as defined in claim 26, where X is H, which is 1,4-dihydro-1-phenylmethylbenzo[c]-1,5-naphthyridin-2(3H)-one.

28. The compound as defined in claim 26, where X is halogen.

29. The compound as defined in claim 26, where X is loweralkoxy.

30. The compound as defined in claim 1, where R₁ is H₂.

31. The compound as defined in claim 30, where R is H.

32. The compound as defined in claim 31, where X is H, which is 1,2,3,4-tetrahydrobenzo[c]-1,5-naphthyridine.

33. The compound as defined in claim 31, where X is halogen.

34. The compound as defined in claim 33, where X is chlorine.

35. The compound as defined in claim 34, where X is 9-chloro, which is 9-chloro-1,2,3,4-tetrahydrobenzo[c]-1,5-naphthyridine.

36. The compound as defined in claim 33, where X is fluorine.

37. The compound as defined in claim 31, where X is loweralkoxy.

38. The compound as defined in claim 37, where X is methoxy.

39. The compound as defined in claim 30, where R is loweralkanoyl.

40. The compound as defined in claim 39, where R is

41. The compound as defined in claim 40, where X is H, which is 1-formyl-1,2,3,4-tetrahydrobenzo[c]-1,5-naphthyridine.

42. The compound as defined in claim 40, where X is halogen.

43. The compound as defined in claim 40, where X is loweralkoxy.

44. The compound as defined in claim 30, where R is arylloweralkanoyl.

45. The compound as defined in claim 44, where R is

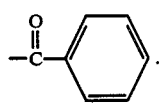

46. The compound as defined in claim 45, where X is H, which is 1-benzoyl-1,2,3,4-tetrahydrobenzo[c]-1,5-naphthyridine.

47. The compound as defined in claim 45, where X is halogen.

48. The compound as defined in claim 45, where X is loweralkoxy.

49. The compound as defined in claim 44, where R is

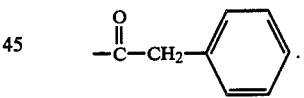

50. The compound as defined in claim 49, where X is H, which is 1-(phenyacetyl)-1,2,3,4-tetrahydrobenzo[c]-1,5-naphthyridine.

51. The compound as defined in claim 49, where X is halogen.

52. The compound as defined in claim 49, where X is loweralkoxy.

53. The compound as defined in claim 30, where R is loweralkyl.

54. The compound as defined in claim 53, where R is methyl.

55. The compound as defined in claim 54, where X is H, which is 1-methyl-1,2,3,4-tetrahydrobenzo[c]-1,5-naphthyridine.

56. The compound as defined in claim 54, where X is halogen.

57. The compound as defined in claim 54, where X is loweralkoxy.

58. The compound as defined in claim 30, where R is arylloweralkyl.

59. The compound as defined in claim 58, where R is

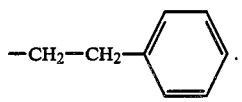

60. The compound as defined in claim 59, where X is H, which is 1-(2-phenylethyl)-1,2,3,4-tetrahydrobenzo[c]-1,5naphthyridine.

61. The compound as defined in claim 59, where X is halogen.

62. The compound as defined in claim 59, where X is loweralkoxy.

63. The compound as defined in claim 58, where R is

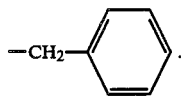

64. The compound as defined in claim 63, where X is H, which is 1-phenylmethyl-1,2,3,4-tetrahydrobenzo[c]-1,5-naphthyridine.

65. A pharmaceutical composition which comprises an effective memory enhancing amount of a compound defined in claim 1.

* * * * *